(12) United States Patent
Finlay et al.

(10) Patent No.: US 7,153,857 B2
(45) Date of Patent: Dec. 26, 2006

(54) ARYLPIPERAZINES AND ARYLPIPERIDINES AND THEIR USE AS METALLOPROTEINASE INHIBITING AGENTS

(75) Inventors: Maurice Raymond Verschoyle Finlay, Macclesfield (GB); Howard Tucker, Macclesfield (GB); David Waterson, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 519 days.

(21) Appl. No.: 10/485,409

(22) PCT Filed: Aug. 8, 2002

(86) PCT No.: PCT/SE02/01436

§ 371 (c)(1),
(2), (4) Date: Jan. 28, 2004

(87) PCT Pub. No.: WO03/014111

PCT Pub. Date: Feb. 20, 2003

(65) Prior Publication Data

US 2004/0220185 A1    Nov. 4, 2004

(30) Foreign Application Priority Data

Aug. 9, 2001 (GB) ................ 0119474.5

(51) Int. Cl.
*A61K 31/496* (2006.01)
*C07D 241/04* (2006.01)

(52) U.S. Cl. .......... 514/252.12; 544/224; 544/336; 544/358; 544/359; 546/184; 546/192; 546/207; 546/210; 514/247; 514/252.1; 514/252.13

(58) Field of Classification Search .......... 544/224, 544/336, 358, 359; 546/184, 192, 207, 210; 514/247, 252.1, 252.12, 252.13
See application file for complete search history.

(56) References Cited

U.S. PATENT DOCUMENTS

| | | | |
|---|---|---|---|
| 5,202,324 A | 4/1993 | Miyake et al. | |
| 5,506,242 A | 4/1996 | MacPherson et al. | |
| 5,552,419 A | 9/1996 | MacPherson et al. | |
| 5,646,167 A | 7/1997 | MacPherson et al. | |
| 5,672,615 A | 9/1997 | MacPherson et al. | |
| 5,817,822 A | 10/1998 | Nantermet et al. | |
| 5,998,412 A | 12/1999 | Broka et al. | |
| 6,057,336 A | 5/2000 | Duan et al. | |
| 6,100,266 A | 8/2000 | Montana et al. | |
| 6,130,220 A | 10/2000 | Broka et al. | |
| 6,143,744 A | 11/2000 | Broka et al. | |
| 6,235,786 B1 | 5/2001 | Dai et al. | |
| 6,294,573 B1 | 9/2001 | Curtin et al. | |
| 6,376,506 B1 | 4/2002 | Broka et al. | |
| 6,479,502 B1 | 11/2002 | Martin | |
| 6,482,827 B1 | 11/2002 | Alpegiani et al. | |
| 6,492,367 B1 * | 12/2002 | DeCrescenzo et al. | 514/252.12 |
| 6,495,568 B1 | 12/2002 | Dack et al. | |
| 6,511,993 B1 * | 1/2003 | Dack et al. ........ | 514/318 |
| 6,610,731 B1 | 8/2003 | Duan et al. | |
| 6,734,183 B1 * | 5/2004 | Barlaam et al. ........ | 514/252.11 |
| 2002/0037900 A1 | 3/2002 | Hannah et al. | |
| 2003/0050310 A1 | 3/2003 | Martin | |
| 2003/0216404 A1 | 11/2003 | Hannah et al. | |

FOREIGN PATENT DOCUMENTS

| | | |
|---|---|---|
| DE | 198 02 350 A1 | 7/1998 |
| EP | 0 381 132 A1 | 8/1990 |
| WO | WO-96/00214 A1 | 1/1996 |
| WO | WO-96/40101 A1 | 12/1996 |
| WO | WO-98/05635 A1 | 2/1998 |
| WO | WO-98/16514 A1 | 4/1998 |
| WO | WO-98/32748 A1 | 7/1998 |
| WO | WO-99/02510 A1 | 1/1999 |
| WO | WO-99/18074 A1 | 4/1999 |
| WO | WO-99/29667 A1 | 6/1999 |
| WO | WO-99/38843 A1 | 8/1999 |
| WO | WO-00/12477 A1 | 3/2000 |
| WO | WO-00/12478 A1 | 3/2000 |
| WO | WO-00/75108 A1 | 12/2000 |
| WO | WO-01/62742 A1 | 8/2001 |
| WO | WO-01/62750 A1 | 8/2001 |
| WO | WO-01/62751 A1 | 8/2001 |
| WO | WO-01/87870 A1 | 11/2001 |
| WO | WO-03/014092 A1 | 2/2003 |
| WO | WO-03/014098 A1 | 2/2003 |

OTHER PUBLICATIONS

US 6,387,931, 05/2002, Dack et al. (withdrawn)

* cited by examiner

*Primary Examiner*—Golam M. M. Shameem
(74) *Attorney, Agent, or Firm*—Fish & Neave IP Group Ropes & Gray LLP

(57) ABSTRACT

Compounds of the formula I

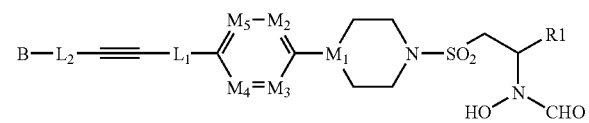

useful as metalloproteinase inhibitors, especially as inhibitors of MMP 13.

19 Claims, No Drawings

ARYLPIPERAZINES AND ARYLPIPERIDINES AND THEIR USE AS METALLOPROTEINASE INHIBITING AGENTS

CROSS-REFERENCE TO RELATED APPLICATIONS

This application is a national stage filing under 35 U.S.C. 371 of International Application No. PCT/SE02/01038, filed May 30, 2002, which claims priority from United Kingdom Patent Application No. 0101980.1, filed Jun. 1, 2001, the specification of which is incorporated by reference herein. International Application No. PCT/SE02/01038 was published under PCT Article 21(2) in English.

FIELD OF THE INVENTION

The present invention relates to compounds useful in the inhibition of metalloproteinases and in particular to pharmaceutical compositions comprising these, as well as their use. In particular, the compounds of this invention are inhibitors of matrix metalloproteinase 13 (MMP13), known also as collagenase 3.

Metalloproteinases are a superfamily of proteinases (enzymes) whose numbers in recent years have increased dramatically. Based on structural and functional considerations these enzymes have been classified into families and subfamilies as described in N. M. Hooper (1994) FEBS Letters 354:1–6. Examples of metalloproteinases include the matrix metalloproteinases (MMPs); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265–279).

Metalloproteinases have been associated with many diseases or conditions. Inhibition of the activity of one or more metalloproteinases may well be of benefit in these diseases or conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atherosclerosis; and chronic obstructive pulmonary diseases, COPD (for example, the role of MMPs such as MMP12 is discussed in Anderson & Shinagawa, 1999, Current Opinion in Anti-inflammatory and Immunomodulatory Investigational Drugs, 1(1): 29–38).

The matrix metalloproteinases (MMPs) are a family of structurally-related zinc-containing endopeptidases which mediate the breakdown of connective tissue macro-molecules. The mammalian MMP family is composed of at least twenty enzymes, classically divided into four sub-groups based on substrate specificity and domain structure [Alexander & Werb (1991) in Hay, E. D. ed. "Cell Biology of the Extracellular Matrix", New York, Plenum Press, 255–302; Murphy & Reynolds (1993) in Royce, P. M. & Steinman, B. eds. "Connective Tissue and its Heritable Disorders", New York, Wiley-Liss Inc., 287–316; Birkedal-Hansen (1995) Curr. Opin. Cell Biol. 7:728–735]. The sub-groups are the collagenases (such as MMP1, MMP8, MMP13), the stromelysins (such as MMP3, MMP10, MMP11), the gelatinases (such as MMP2, MMP9) and the membrane-type MMPs (such as MMP14, MMP15, MMP16, MMP17). Enzyme activity is normally regulated in vivo by tissue inhibitors of metalloproteinases (TIMPs).

Because of their central role in re-modelling connective tissue, both as part of normal physiological growth and repair and as part of disease processes, there has been substantial interest in these proteins as targets for therapeutic intervention in a wide range of degenerative and inflammatory diseases, such as arthritis, atherosclerosis, and cancer (Whittaker et al (1999) Chem. Rev. 99:2735–2776).

A number of MMP inhibitor compounds are known and some are being developed for pharmaceutical uses (see for example the review by Beckett & Whittaker (1998) Exp. Opin. Ther. Patents, 8(3):259–282). Different classes of compounds may have different degrees of potency and selectivity for inhibiting various MMPs. Whittaker M. et al (1999, Chem. Rev. 99:2735–2776) review a wide range of known MMP inhibitor compounds. They state that an effective MMP inhibitor requires a zinc binding group or ZBG (functional group capable of chelating the active site zinc(II) ion), at least one functional group which provides a hydrogen bond interaction with the enzyme backbone, and one or more side chains which undergo effective van der Waals interactions with the enzyme subsites. Zinc binding groups in known MMP inhibitors include hydroxamic acids (—C(O)NHOH), reverse hydroxamates (—N(OH)CHO), thiols, carboxylates and phosphonic acids.

We have discovered a new class of compounds that are inhibitors of metalloproteinases and are of particular interest in inhibiting MMP13. The compounds of this invention have beneficial potency and/or pharmacokinetic properties. In particular they show selectivity for MMP13.

MMP13, or collagenase 3, was initially cloned from a cDNA library derived from a breast tumour [J. M. P. Freije et al. (1994) Journal of Biological Chemistry 269(24): 16766–16773]. PCR-RNA analysis of RNAs from a wide range of tissues indicated that MMP13 expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation MMP13 has been detected in transformed epidermal keratinocytes [N. Johansson et al., (1997) Cell Growth Differ. 8(2):243–250], squamous cell carcinomas [N. Johansson et al., (1997) Am. J. Pathol. 151(2):499–508] and epidermal tumours [K. Airola et al., (1997) J. Invest. Dermatol. 109(2):225–231]. These results are suggestive that MMP13 is secreted by transformed epithelial cells and may be involved in the extracellular matrix degradation and cell-matrix interaction associated with metastasis especially as observed in invasive breast cancer lesions and in malignant epithelia growth in skin carcinogenesis.

Recent published data implies that MMP13 plays a role in the turnover of other connective tissues. For instance, consistent with MMP13's substrate specificity and preference for degrading type II collagen [P. G. Mitchell et al., (1996) J. Clin. Invest. 97(3):761–768; V. Knauper et al., (1996) The Biochemical Journal 271:1544–1550], MMP13 has been hypothesised to serve a role during primary ossification and skeletal remodelling [M. Stahle-Backdahl et al., (1997) Lab. Invest. 76(5):717–728; N. Johansson et al., (1997) Dev. Dyn. 208(3):387–397], in destructive joint diseases such as rheumatoid and osteo-arthritis [D. Wernicke et al., (1996) J. Rheumatol. 23:590–595; P. G. Mitchell et al., (1996) J. Clin. Invest. 97(3):761–768; O. Lindy et al., (1997) Arthritis Rheum 40(8): 1391–1399]; and during the aseptic loosening of hip replacements [S. Imai et al., (1998) J. Bone Joint Surg. Br. 80(4):701–710]. MMP13 has also been implicated in chronic adult periodontitis as it has been localised to the epithelium of chronically inflamed mucosa human gingival tissue [V. J. Uitto et al., (1998) Am. J. Pathol 152(6): 1489–1499] and in remodelling of the collagenous matrix in chronic wounds [M. Vaalamo et al., (1997) J. Invest. Dermatol. 109(1):96–101].

U.S. Pat. No. 6,100,266 and WO-99/38843 disclose compounds of the general formula

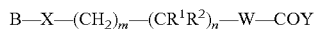

for use in the manufacture of a medicament for the treatment or prevention of a condition associated with matrix metalloproteinases. Specifically disclosed is the compound N-{1S-[4-(4-Chlorophenyl)piperazine-1-sulfonylmethyl]-2-methylpropyl}-N-hydroxyformamide.

WO-00/12478 discloses arylpiperazines that are matrix metalloproteinase inhibitors, including compounds with an hydroxamic acid zinc binding group and compounds with a reverse hydroxamate zinc binding group.

We have now discovered compounds that are potent MMP13 inhibitors and have desirable activity profiles.

In a first aspect of the invention we now provide a compound of the formula I

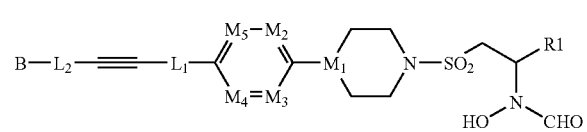

wherein

B is selected from H, $C_{1-6}$alkyl, up to $C_{1-2}$ cycloalkyl, up to $C_{1-2}$ aryl, and up to $C_{1-2}$ heteroaryl;

B is optionally substituted by up to three groups independently selected from OH, $NO_2$, $CF_3$, CN, halogen, $SC_{1-4}$alkyl, $SOC_{1-4}$alkyl, $SO_2C_{1-4}$alkyl, $C_{1-4}$alkyl, $C_{1-4}$alkoxy;

$L_1$ and $L_2$ are each independently selected from a direct bond and $C_{1-6}$alkyl;

$M_1$, $M_2$, $M_3$, $M_4$ and $M_5$ are each independently selected from N and C;

R1 is the group —X—Y;

X is $C_{1-6}$alkyl;

Y is selected from up to C10 cycloalkyl, up to C10 aryl, and up to C10 heteroaryl;

Y is optionally substituted by up to three groups independently selected from OH, $NO_2$, $CF_3$, CN, halogen, $SC_{1-4}$alkyl, $SOC_{1-4}$alkyl, $SO_2C_{1-4}$alkyl, $C_{1-4}$alkyl, $C_{1-4}$alkoxy;

Any alkyl group outlined above may be straight chain or branched;

Any heteroaryl group outlined above is an aromatic ring containing one or more heteroatoms independently selected from N, O, S.

In a further aspect of the invention we provide compounds of the formula II

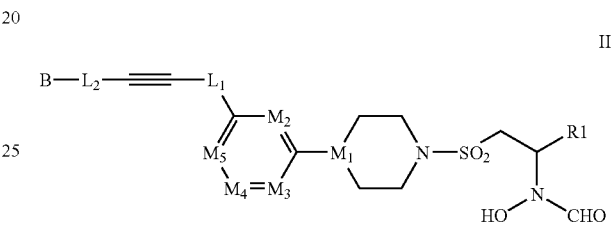

wherein B, $L_1$, $L_2$, $M_1$, $M_2$, $M_3$, $M_4$, $M_5$, R1, X and Y are as defined above for the compound of formula I.

Preferred compounds of the formulae I or II are those wherein any one or more of the following apply:

B is selected from H, $C_{1-6}$alkyl, C6 aryl, and up to C6 heteroaryl; preferably B is H, $C_{2-4}$alkyl, C6 aryl, and up to C6 heteroaryl; most preferably B is up to C6 heteroaryl;

B is not substituted or is substituted by at least one group selected from $CF_3$, CN, halogen (preferably fluoro or chloro), $C_{1-4}$alkyl;

At least one of $L_1$ and $L_2$ is a direct bond; preferably each of $L_1$ and $L_2$ is a direct bond;

$M_1$ is N;

At least one of $M_2$, $M_3$, $M_4$, $M_5$ is C, and at least one of $M_2$, $M_3$, $M_4$, $M_5$ is N; preferably each of $M_4$ and $M_5$ is C, and at least one of $M_2$ and $M_3$ is N; most preferably each of $M_4$ and $M_5$ is C, $M_2$ is C or N and $M_3$ is N;

X is $C_{2-5}$alkyl; preferably X is $C_{2-3}$alkyl;

Y is C6 aryl or C6 heteroaryl; preferably Y is phenyl, pyridyl, pyrimidinyl, or pyrazinyl; most preferably Y is pyrimidinyl;

Y is not substituted or is substituted by at least one halogen group (preferably fluoro or chloro).

For example, preferred compounds of the invention include those wherein B is phenyl, pyridyl, pyrimidinyl, or thienyl.

Other preferred compounds include those wherein $L_1$ is a direct bond, $L_2$ is a direct bond, $M_1$ is N, $M_2$ is C or N, $M_3$ is N, $M_4$ is C, and $M_5$ is C.

Other preferred compounds include those wherein R1 is 3- or 4-chlorophenylethyl, 3- or 4-chlorophenylpropyl, 2- or 3-pyridylethyl, 2- or 3-pyridylpropyl, 2- or 4-pyrimidinylethyl (optionally monosubstituted by fluoro or chloro), 2- or 4-pyrimidinylpropyl (optionally monosubstituted by fluoro or chloro), 2-(2-pyrimidinyl)ethyl (optionally monosubstitued by fluoro or chloro), 2-(2-pyrimidinyl)propyl (optionally monosubstitued by fluoro or chloro). Particularly preferred compounds include those wherein R1 is 2-pyrimidinylpropyl, 2-pyrimidinylethyl or 5-fluoro-2-pyrimidinylethyl.

It will be appreciated that the particular substituents and number of substituents on B and/or R1 are selected so as to avoid sterically undesirable combinations.

Each exemplified compound represents a particular and independent aspect of the invention.

Where optically active centres exist in the compounds of formulae I or II, we disclose all individual optically active forms and combinations of these as individual specific embodiments of the invention, as well as their corresponding racemates.

It will be appreciated that the compounds according to the invention can contain one or more asymmetrically substituted carbon atoms. The presence of one or more of these asymmetric centres (chiral centres) in a compound of formulae I or II can give rise to stereoisomers, and in each case the invention is to be understood to extend to all such stereoisomers, including enantiomers and diastereomers, and mixtures including racemic mixtures thereof.

Where tautomers exist in the compounds of formulae I or II, we disclose all individual tautomeric forms and combinations of these as individual specific embodiments of the invention.

As previously outlined the compounds of the invention are metalloproteinase inhibitors, in particular they are inhibitors of MMP13. Each of the above indications for the compounds of the formulae I or II represents an independent and particular embodiment of the invention. Whilst we do not wish to be bound by theoretical considerations, the compounds of the invention are believed to show selective inhibition for any one of the above indications relative to any MMP1 inhibitory activity, by way of non-limiting example they may show 100–1000 fold selectivity over any MMP1 inhibitory activity.

The compounds of the invention may be provided as pharmaceutically acceptable salts. These include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

They may also be provided as in vivo hydrolysable esters. These are pharmaceutically acceptable esters that hydrolyse in the human body to produce the parent compound. Such esters can be identified by administering, for example intravenously to a test animal, the compound under test and subsequently examining the test animal's body fluids. Suitable in vivo hydrolysable esters for carboxy include methoxymethyl and for hydroxy include formyl and acetyl, especially acetyl.

In order to use a compound of the formulae I or II or a pharmaceutically acceptable salt or in vivo hydrolysable ester thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formulae I or II or a pharmaceutically acceptable salt or an in vivo hydrolysable ester and pharmaceutically acceptable carrier.

The pharmaceutical compositions of this invention may be administered in standard manner for the disease or condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more diseases or conditions referred to hereinabove.

The pharmaceutical compositions of this invention will normally be administered to humans so that, for example, a daily dose of 0.5 to 75 mg/kg body weight (and preferably of 0.5 to 30 mg/kg body weight) is received. This daily dose may be given in divided doses as necessary, the precise amount of the compound received and the route of administration depending on the weight, age and sex of the patient being treated and on the particular disease or condition being treated according to principles known in the art.

Typically unit dosage forms will contain about 1 mg to 500 mg of a compound of this invention.

Therefore in a further aspect, the present invention provides a compound of the formulae I or II or a pharmaceutically acceptable salt or in vivo hydrolysable ester thereof for use in a method of therapeutic treatment of the human or animal body. In particular we disclose use in the treatment of a disease or condition mediated by MMP13.

In yet a further aspect the present invention provides a method of treating a metalloproteinase mediated disease or condition which comprises administering to a warm-blooded animal a therapeutically effective amount of a compound of the formulae I or II or a pharmaceutically acceptable salt or in vivo hydrolysable ester thereof. Metalloproteinase mediated diseases or conditions include arthritis (such as osteoarthritis), atherosclerosis, chronic obstructive pulmonary diseases (COPD).

In another aspect the present invention provides a process for preparing a compound of the formulae I or II or a pharmaceutically acceptable salt or in vivo hydrolysable ester thereof which process is outlined below.

A compound of the formula I can be prepared from a compound of the formula III by reaction with hydroxylamine followed by formylation.

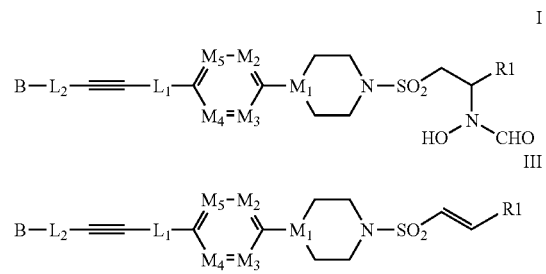

A compound of the formula III can be prepared from a compound of the formula IV and a compound of the formula V or from a compound of the formula VI and a compound of the formula VII. A compound of the formula V may be prepared from a compound of the formula VII.

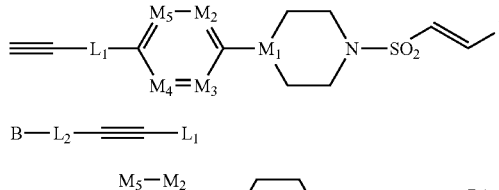

IV

V

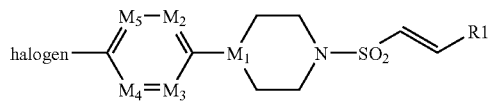

VI

VII

A compound of the formula VII may be prepared from a compound of the formula VIII by reaction with a suitable aldehyde (R1CHO) or a suitable ester (R1COOR). A compound of formula VIII may be conviniently prepared from a compound of formula IX. A compound of the formula IX can be prepared conveniently from a compound of the formula X and a compound of the formula XI (where P is hydrogen or a suitable protecting group and $M_1'$ is hydrogen or a suitably reactive group).

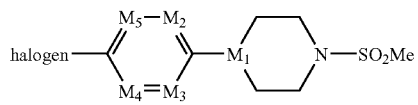

VIII

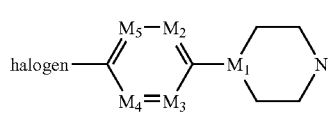

IX

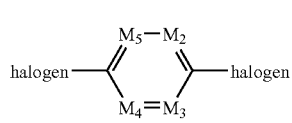

X

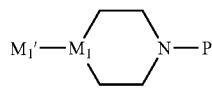

XI

A compound of the formula III can also be prepared from a compound of the formula XII by reaction with a suitable aldehyde (R1CHO) or a suitable ester (R1COOR). A compound of the formula XII can be prepared conveniently from a compound of the formula XIII and a compound of the formula XIV

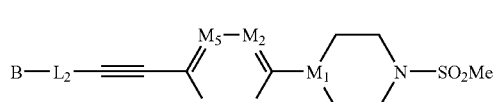

XII

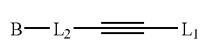

XIII

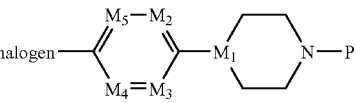

XIV

A compound of the formula II may be prepared from a compound of the formula XV by similar methodology to that described for compound I above.

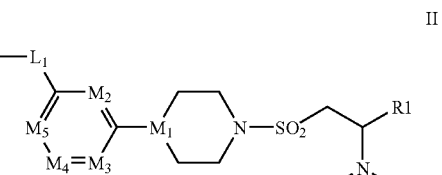

II

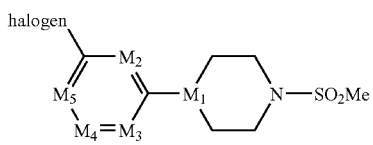

XV

It will be appreciated that many of the relevant starting materials are commercially available or may be made by any convenient method as described in the literature or known to the skilled chemist or described in the Examples herein.

The compounds of the invention may be evaluated for example in the following assays:

Isolated Enzyme Assays

Matrix Metalloproteinase Family Including for Example MMP13.

Recombinant human proMMP13 may be expressed and purified as described by Knauper et al. [V. Knauper et al., (1996) The Biochemical Journal 271:1544–1550 (1996)]. The purified enzyme can be used to monitor inhibitors of activity as follows: purified proMMP13 is activated using 1 mM amino phenyl mercuric acid (APMA), 20 hours at 21° C.; the activated MMP13 (11.25 ng per assay) is incubated for 4–5 hours at 35° C. in assay buffer (0.1M Tris-HCl, pH 7.5 containing 0.1M NaCl, 20 mM CaCl2, 0.02 mM ZnCl and 0.05% (w/v) Brij 35 using the synthetic substrate 7-methoxycoumarin-4-yl)acetyl.Pro.Leu.Gly.Leu.N-3-(2,4-dinitrophenyl)-L-2,3-diaminopropionyl.Ala.Arg.$NH_2$ in the presence or absence of inhibitors. Activity is determined by measuring the fluorescence at λex 328 nm and λem 393 nm. Percent inhibition is calculated as follows: % Inhibition is equal to the [Fluorescence$_{plus\ inhibitor}$–Fluorescence$_{background}$] divided by the [Fluorescence$_{minus\ inhibitor}$–Fluorescence$_{background}$].

A similar protocol can be used for other expressed and purified pro MMPs using substrates and buffers conditions optimal for the particular MMP, for instance as described in C. Graham Knight et al., (1992) FEBS Lett. 296(3):263–266.

Adamalysin Family Including for Example TNF Convertase

The ability of the compounds to inhibit proTNFα convertase enzyme may be assessed using a partially purified, isolated enzyme assay, the enzyme being obtained from the membranes of THP-1 as described by K. M. Mohler et al., (1994) Nature 370:218–220. The purified enzyme activity and inhibition thereof is determined by incubating the partially purified enzyme in the presence or absence of test compounds using the substrate 4',5'-Dimethoxy-fluoresceinyl Ser.Pro.Leu.Ala.Gln.Ala.Val.Arg.Ser.Ser.Ser.Arg.Cys (4-(3-succinimid-1-yl)-fluorescein)-NH$_2$ in assay buffer (50 mM Tris HCl, pH 7.4 containing 0.1% (w/v) Triton X-100 and 2 mM CaCl$_2$), at 26° C. for 18 hours. The amount of inhibition is determined as for MMP13 except λex 490 nm and λem 530 nm were used. The substrate was synthesised as follows. The peptidic part of the substrate was assembled on Fmoc-NH-Rink-MBHA-polystyrene resin either manually or on an automated peptide synthesiser by standard methods involving the use of Fmoc-amino acids and O-benzotriazol-1-yl-N,N,N',N'-tetramethyluronium hexafluorophosphate (HBTU) as coupling agent with at least a 4- or 5-fold excess of Fmoc-amino acid and HBTU. Ser$^1$ and Pro$^2$ were double-coupled. The following side chain protection strategy was employed; Ser$^1$(But), Gln$^5$(Trityl), Arg$^{8,12}$ (Pmc or Pbf), Ser$^{9,10,11}$(Trityl), Cys$^{13}$(Trityl). Following assembly, the N-terminal Fmoc-protecting group was removed by treating the Fmoc-peptidyl-resin with 20% piperidine in DMF. The amino-peptidyl-resin so obtained was acylated by treatment for 1.5–2 hr at 70° C. with 1.5–2 equivalents of 4',5'-dimethoxy-fluorescein-4(5)-carboxylic acid [Khanna & Ullman, (1980) Anal Biochem. 108:156–161) which had been preactivated with diisopropylcarbodiimide and 1-hydroxybenzotriazole in DMF]. The dimethoxyfluoresceinyl-peptide was then simultaneously deprotected and cleaved from the resin by treatment with trifluoroacetic acid containing 5% each of water and triethylsilane. The dimethoxyfluoresceinyl-peptide was isolated by evaporation, trituration with diethyl ether and filtration. The isolated peptide was reacted with 4-(N-maleimido)-fluorescein in DMF containing diisopropylethylamine, the product purified by RP-HPLC and finally isolated by freeze-drying from aqueous acetic acid. The product was characterised by MALDI-TOF MS and amino acid analysis.

Natural Substrates

The activity of the compounds of the invention as inhibitors of aggrecan degradation may be assayed using methods for example based on the disclosures of E. C. Arner et al., (1998) Osteoarthritis and Cartilage 6:214–228; (1999) Journal of Biological Chemistry, 274 (10), 6594–6601 and the antibodies described therein. The potency of compounds to act as inhibitors against collagenases can be determined as described by T. Cawston and A. Barrett (1979) Anal. Biochem. 99:340–345.

Inhibition of Metalloproteinase Activity in Cell/Tissue Based Activity Test as an Agent to Inhibit Membrane Sheddases Such as TNF Convertase The ability of the compounds of this invention to inhibit the cellular processing of TNFα production may be assessed in THP-1 cells using an ELISA to detect released TNF essentially as described K. M. Mohler et al., (1994) Nature 370:218–220. In a similar fashion the processing or shedding of other membrane molecules such as those described in N. M. Hooper et al., (1997) Biochem. J. 321:265–279 may be tested using appropriate cell lines and with suitable antibodies to detect the shed protein.

Test as an Agent to Inhibit Cell Based Invasion

The ability of the compound of this invention to inhibit the migration of cells in an invasion assay may be determined as described in A. Albini et al., (1987) Cancer Research 47:3239–3245.

Test as an Agent to Inhibit Whole Blood TNF Sheddase Activity

The ability of the compounds of this invention to inhibit TNFα production is assessed in a human whole blood assay where LPS is used to stimulate the release of TNFα. Heparinized (10 Units/mL) human blood obtained from volunteers is diluted 1:5 with medium (RPMI1640+bicarbonate, penicillin, streptomycin and glutamine) and incubated (160 μl) with 20 μl of test compound (triplicates), in DMSO or appropriate vehicle, for 30 min at 37° C. in a humidified (5% $CO_2$/95% air) incubator, prior to addition of 20 μl LPS (E. coli. 0111:B4; final concentration 10 μg/mL). Each assay includes controls of diluted blood incubated with medium alone (6 wells/plate) or a known TNFα inhibitor as standard. The plates are then incubated for 6 hours at 37° C. (humidified incubator), centrifuged (2000 rpm for 10 min; 4° C.), plasma harvested (50–100 μl) and stored in 96 well plates at −70° C. before subsequent analysis for TNFα concentration by ELISA.

Test as an Agent to Inhibit in vitro Cartilage Degradation

The ability of the compounds of this invention to inhibit the degradation of the aggrecan or collagen components of cartilage can be assessed essentially as described by K. M. Bottomley et al., (1997) Biochem J. 323:483–488.

Pharmacodynamic Test

To evaluate the clearance properties and bioavailability of the compounds of this invention an ex vivo pharmacodynamic test is employed which utilises the synthetic substrate assays above or alternatively HPLC or Mass spectrometric analysis. This is a generic test which can be used to estimate the clearance rate of compounds across a range of species. Animals (e.g. rats, marmosets) are dosed iv or po with a soluble formulation of compound (such as 20% w/v DMSO, 60% w/v PEG400) and at subsequent time points (e.g. 5, 15, 30, 60, 120, 240, 480, 720, 1220 mins) the blood samples are taken from an appropriate vessel into 10 U heparin. Plasma fractions are obtained following centrifugation and the plasma proteins precipitated with acetonitrile (80% w/v final concentration). After 30 mins at −20° C. the plasma proteins are sedimented by centrifugation and the supernatant fraction is evaporated to dryness using a Savant speed vac. The sediment is reconstituted in assay buffer and subsequently analysed for compound content using the synthetic substrate assay. Briefly, a compound concentration-response curve is constructed for the compound undergoing evaluation. Serial dilutions of the reconstituted plasma extracts are assessed for activity and the amount of compound present in the original plasma sample is calculated using the concentration-response curve taking into account the total plasma dilution factor.

In vivo Assessment

Test as an Anti-TNF Agent

The ability of the compounds of this invention as ex vivo TNFα inhibitors is assessed in the rat. Briefly, groups of male Wistar Alderley Park (AP) rats (180–210 g) are dosed with compound (6 rats) or drug vehicle (10 rats) by the appropriate route e.g. peroral (p.o.), intraperitoneal (i.p.), subcutaneous (s.c.). Ninety minutes later rats are sacrificed using a rising concentration of $CO_2$ and bled out via the posterior vena cavae into 5 Units of sodium heparin/mL blood. Blood samples are immediately placed on ice and centrifuged at 2000 rpm for 10 min at 4° C. and the harvested plasmas frozen at −20° C. for subsequent assay of their effect on TNFα production by LPS-stimulated human blood. The rat plasma samples are thawed and 175 μl of each sample are added to a set format pattern in a 96 well plate. Fifty μl of heparinized human blood is then added to each well, mixed and the plate is incubated for 30 min at 37° C. (humidified incubator). LPS (25 μl; final concentration 10 μg/mL) is added to the wells and incubation continued for a further 5.5 hours. Control wells are incubated with 25 μl of medium alone. Plates are then centrifuged for 10 min at 2000 rpm and 200 μL of the supernatants are transferred to a 96 well plate and frozen at −20° C. for subsequent analysis of TNF concentration by ELISA.

Data analysis by dedicated software calculates for each compound/dose:

Percent inhibition of TNFα=Mean TNFα(Controls)−
Mean TNFα(Treated)×100

Test as an Anti-arthritic Agent

Activity of a compound as an anti-arthritic is tested in the collagen-induced arthritis (CIA) as defined by D. E. Trentham et al., (1977) J. Exp. Med. 146,:857. In this model acid soluble native type II collagen causes polyarthritis in rats when administered in Freunds incomplete adjuvant. Similar conditions can be used to induce arthritis in mice and primates.

Test as an Anti-cancer Agent

Activity of a compound as an anti-cancer agent may be assessed essentially as described in I. J. Fidler (1978) Methods in Cancer Research 15:399–439, using for example the B16 cell line (described in B. Hibner et al., Abstract 283 p75 10th NCI-EORTC Symposium, Amsterdam Jun. 16–19 1998).

The invention will now be illustrated but not limited by the following Examples:

EXAMPLE 1 hydroxy{-1-[({4-[5-(pyridin-2-ylethynyl)pyridin-2-yl]piperazin-1-yl}sulfonyl)methyl]-4-pyrimidin-2-ylbutyl}formamide

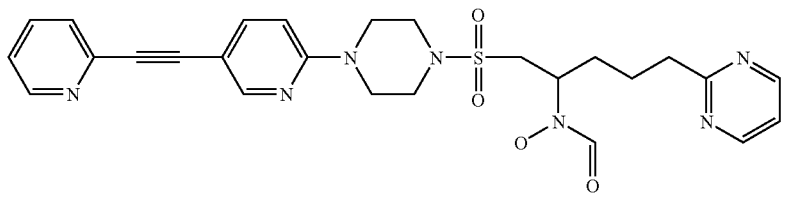

To formic acid (1.5 mL, 39 mmol) at 0° C. was added acetic anhydride (375 μL, 3.9 mmol) and the mixture was stirred at RT for 10 minutes. The reaction was then recooled to 0° C., and a solution of 2-[4-(hydroxyamino)-5-({4-[5-(pyridin-2-ylethynyl)pyridin-2-yl]piperazin-1-yl}sulfonyl) pentyl]pyrimidine (403 mg, 0.79 mmol) in THF (8 mL) was then added. The reaction was brought to RT and stirred for one hour. Volatiles were then removed in vacuo, and the residue azeotroped with toluene (2×5 mL). The residue was then dissolved in MeOH (10 mL) and heated to 40° C. for one hour. The solution was then cooled to RT and concentrated in vacuo. The residue was then purified by flash chromatography (silica gel, 10% MeOH in EtOAc) to give the title compound as a pale yellow foam (231 mg, 0.43 mmol, 54%).

$^1$H NMR (DMSO-D6, 373K): 9.41 (br s, 1H), 8.65 (d, 2H), 8.56 (d, 1H), 8.36 (d, 1H), 8.11 (br s, 1H), 7.79 (m, 1H), 7.71 (dd, 1H), 7.55 (d, 1H), 7.32 (m, 1H), 7.28 (dd, 1H), 6.88 (d, 1H), 3.72 (m, 4H), 3.45 (dd, 1H), 3.32 (m, 4H), 3.17 (dd, 1H), 2.92 (m, 3H), 1.77 (m, 4H)

MS (ESI): 536.45 (MH$^+$)

The starting material was prepared as follows:

To a stirred solution of 2-chloro-5-iodo-pyridine (CAS number 69045-79-0, 10.52 g, 43.9 mmol) and diisopropylethylamine (11.5 mL, 65.9 mmol) in DMA (200 mL) was added piperazine (15.14 g, 0.176 mol). The mixture was then heated to 120° C. for 20 hours. The solid precipitate was then filtered off, and the filtrate evaporated in vacuo. The residue was partitioned between EtOAc (100 mL) and water (100 mL) and the layers were separated. The aqueous layer was then extracted with EtOAc (2×100 mL). The combined organic extracts were then dried, (MgSO$_4$), filtered and concentrated in vacuo, to give 1-(5-iodopyridin-2-yl)piperazine as a yellow solid (10.42 g, 36 mmol, 82%).

$^1$H NMR (CDCl$_3$): 8.30 (d, 1H), 7.65 (dd, 1H), 6.45 (d, 1H), 3.46, (t, 4H), 2.97 (t, 4H).

MS (ESI): 290.29 (MH$^+$).

To a stirred solution of 1-(5-iodopyridin-2-yl)piperazine (CAS number 219635-89-9, 10.42 g, 36 mmol), in CH$_2$Cl$_2$ (150 mL) at 0° C. was added a solution of BOC—O—BOC (7.87 g, 26 mmol). The reaction was allowed to warm to RT and was stirred for 18 hours. Volatiles were removed in vacuo, and the residue was dissolved in EtOAc (200 mL). The solution was washed with water (100 mL), and the aqueous layer was extracted with EtOAc (2×100 mL). The combined organic extracts were then dried, (MgSO$_4$), filtered and concentrated in vacuo, to give tert-butyl 4-(5-iodopyridin-2-yl)piperazine-1-carboxylate as a yellow solid (14 g, 36 mmol, 99%).

$^1$H NMR (CDCl$_3$): 8.31 (d, 1H), 7.08 (dd, 1H), 6.46 (d, 1H), 3.50 (s, 8H), 1.48 (s, 9H).

MS (ESI): 390.37 (MH$^+$)

To a stirred solution of tert-butyl 4-(5-iodopyridin-2-yl) piperazine-1-carboxylate (4.087 g, 10.5 mmol) in DMA (75 mL) at RT was added 2-ethynylpyridine, (CAS number 1945-84-2, 1.17 mL, 11.5 mmol), triethylamine (4.4 mL, 31.5 mmol), CuI (800 mg, 4.2 mmol) and Pd(PPh$_3$)$_4$ (1.21 g, 1.05 mmol). After stirring for 30 minutes, the DMA was removed in vacuo, and the residue diluted with EtOAc (100 mL). The dark solution was then washed with water (100 mL). The layers were separated and the aqueous phase extracted with EtOAc (3×50 mL). The combined organic extracts were then dried, (MgSO$_4$), filtered and concentrated in vacuo. The residue was then purified by flash chromatography (silica gel, 50% EtOAc in hexanes) to give tert-butyl 4-[5-(pyridin-2-ylethynyl)pyridin-2-yl]piperazine-1-carboxylate as a brown oil (3.8 g, 10.5 mmol, 99%).

¹H NMR (CDCl₃): 8.62 (m, 1H), 8.43 (d, 1H), 7.68 (m, 2H), 7.49 (d, 1H), 7.21 (dd, 1H), 6.58 (d, 1H), 3.61 (m, 8H), 1.51 (s, 9H).

MS (ESI): 364.94 (MH⁺)

To a stirred solution of tert-butyl 4-[5-(pyridin-2-ylethynyl)pyridin-2-yl]piperazine-1-carboxylate (3.8 g, 10.4 mmol) in CH₂Cl₂ (35 mL) at 0° C. was added trifluoroacetic acid (17.2 mL). The reaction was brought to room temperature and stirred for 30 minutes. Volatiles were removed in vacuo, and the residue was azeotroped with toluene (2×10 mL). The residue was then dissolved in CH₂Cl₂ and washed with aqueous sodium hydroxide solution (2M, 2×20 mL). The layers were then separated and the aqueous phase extracted with CH₂Cl₂ (3×10 mL). The combined organic extracts were then dried, (MgSO₄), filtered and concentrated in vacuo. The residue was dissolved in CH₂Cl₂ (50 mL), and cooled to 0° C. and treated sequentially with triethylamine (1.5 mL, 16.7 mmol) and methanesulfonyl chloride (1.1 mL, 13.5 mmol). The reaction was brought to RT and stirred for 1 hour. The reaction was then quenched with water (50 mL). The layers were separated and the aqueous phase extracted with CH₂Cl₂ (3×20 mL). The combined organic extracts were then dried, (MgSO₄), filtered and concentrated in vacuo. The residue was then purified by flash chromatography (silica gel, 10% MeOH in EtoAc) to give 1-(methylsulfonyl)-4-[5-(pyridin-2-ylethynyl)pyridin-2-yl]piperazine as a brown solid (3.5 g, 10.2 mmol, 98%).

¹H NMR (CDCl₃): 8.60 (d, 1H), 8.46 (d, 1H), 7.69, (m, 2H), 7.52 (d, 1H), 7.23 (m, 1H), 6.65 (d, 1H), 3.79 (m, 4H), 3.35 (m, 4H), 2.83 (s, 3H).

MS (ESI): 342.83 (MH⁺)

To a stirred suspension of 1-(methylsulfonyl)-4-[5-(pyridin-2-ylethynyl)pyridin-2-yl]piperazine (456 mg, 1.33 mmol) in THF (10 mL) at −20° C., was added dropwise a solution of LiHMDS in THF (3.0 mL, 11.0M solution, 3.0 mmol). The resulting suspension was stirred at −20° C. for 30 minutes before being treated with diethyl chlorophosphate (212 µL, 1.46 mmol). The solution was then maintained at −20° C. for 15 minutes before being treated with a solution of 4-pyrimidin-2-ylbutanal (220 mg, 1.46 mmol, CAS number 260441-10-9) in THF (3 mL). The solution was stirred at −20° C. for a further 20 minutes before being quenched with saturated aqueous ammonium chloride solution (10 mL). The layers were separated and the aqueous phase extracted with ethyl acetate (3×10 mL). The combined organic extracts were then dried, (MgSO₄), filtered and concentrated in vacuo to give -[(4E/Z)-5-({4-[5-(pyridin-2-ylethynyl)pyridin-2-yl]piperazin-1-yl}sulfonyl)pent-4-enyl]pyrimidine. This material was used crude in the next step.

MS (ESI): 474.97 (MH⁺)

To a stirred solution of 2-[(4E/Z)-5-({4-[5-(pyridin-2-ylethynyl)pyridin-2-yl]piperazin-1-yl}sulfonyl)pent-4-enyl]pyrimidine (crude from previous step), in THF (15 mL) at RT was added a solution of hydroxylamine (3 mL, 50% aqueous solution in water). The reaction was stirred for 3 hours at RT before being quenched with saturated aqueous ammonium chloride solution (5 mL). The layers were separated and the aqueous phase extracted with ethyl acetate (3×10 mL). The combined organic extracts were then dried, (MgSO₄), filtered and concentrated in vacuo. The residue was then purified by flash chromatography (silica, 10% MeOH in ethyl acetate) to give 2-[4-(hydroxyamino)-5-({4-[5-(pyridin-2-ylethynyl)pyridin-2-yl]piperazin-1-yl}sulfonyl)pentyl]pyrimidine (403 mg, 0.79 mmol).

MS (ESI): 508.22 (MH⁺)

EXAMPLE 2 hydroxy[4-pyrimidin-2-yl-1-({[4-(5-{[5-(trifluoromethyl)pyridin-2-yl]ethynyl}pyridin-2-yl)piperazin-1-yl]sulfonyl}methyl)butyl]formamide

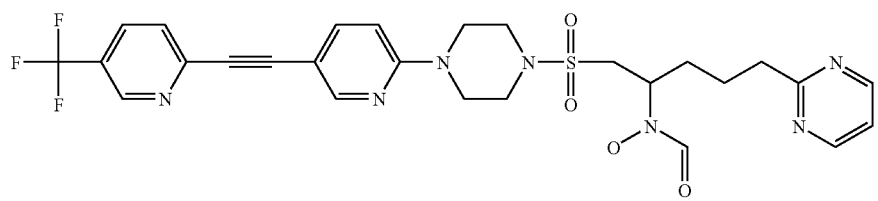

To formic acid (0.36 mL, 9.5 mmol) at 0° C. was added acetic anhydride (90 µL, 0.95 mmol) and the mixture was stirred at RT for 10 minutes. The reaction was then recooled to 0° C., and added to a solution of 2-(4-(hydroxyamino)-5-{[4-(5-{[5-(trifluoromethyl)pyridin-2-yl]ethynyl}pyridin-2-yl)piperazin-1-yl]sulfonyl}pentyl)pyrimidine (403 mg, 0.79 mmol) and formic acid (0.36 mL, 9.5 mmol) in THF (3 mL) at 0° C. The reaction was brought to RT and stirred for one hour. Volatiles were then removed in vacuo, and the residue azeotroped with toluene (2×5 mL). The residue was then dissolved in MeOH (10 mL) and heated to 40° C. for one hour. The solution was then cooled to RT and concentrated in vacuo. The residue was then purified by flash chromatography (silica gel, 10% MeOH in EtOAc) to give the title compound as a pale yellow foam (66 mg, 0.11 mmol, 58%).

¹H NMR (DMSO-D6, 373K): 9.38 (br s, 1H), 8.90 (d, 1H), 8.67 (d, 2H), 8.42 (d, 1H), 8.15 (dd, 1H), 8.14 (br s, 1H), 7.73 (m, 2H), 7.27 (t, 1H), 6.90 (d, 1H), 3.71 (m, 4H), 3.42 (dd, 1H), 3.30 (m, 4H), 3.16 (dd, 1H), 2.88 (m, 3H), 1.76 (m, 3H), 1.66 (m, 1H)

MS (ESI): 604.39 (MH⁺)

The starting material was prepared as follows:

To a stirred solution of tert-butyl 4-(5-iodopyridin-2-yl)piperazine-1-carboxylate (1.0 g, 2.57 mmol, prepared as in Example 1), trimethylsilyl acetylene (0.73 mL, 5.14 mmol), triethylamine (1.11 mL, 7.71 mmol), and cuprous iodide (196 mg, 1.03 mmol) in DMA (20 mL) at 25° C. was added tetrakistriphenylphosphine palladium (0) (149 mg, 5 mol %). The reaction was stirred for 10 minutes. Volatiles were removed in vacuo. The residue was then dissolved in ethyl acetate (250 mL) and washed with water (100 mL). The layers were then separated and the aqueous phase extracted with ethyl acetate (250 mL). The combined organic extracts were then dried, (MgSO₄), filtered and concentrated in vacuo. The residue was then purified by flash chromatography (silica gel, 10% EtOAc in hexanes) to give tert-butyl 4-{5-[(trimethylsilyl)ethynyl]pyridin-2-yl}piperazine-1-carboxylate as a pale brown solid (652 mg, 1.81 mmol, 70%).

$^1$H NMR (CDCl$_3$): 8.28 (d, 1H), 7.50 (dd, 1H), 6.50 (d, 1H), 3.57 (m, 8H), 1.49 (s, 9H), 0.25 (s, 9H).

MS (ESI): 360.51 (MH$^+$).

To a stirred solution of tert-butyl 4-{5-[(trimethylsilyl)ethynyl]pyridin-2-yl}piperazine-1-carboxylate (637 mg, 1.77 mmol), in THF (8 mL) at 25° C. was added tetrabutylammonium fluoride (1.77 mL, 1.0M in THF). The reaction was stirred for 1 hour. Water (5 mL) was then added and product extracted with ethyl acetate (2×5 mL). The combined organic extracts were then dried, (MgSO$_4$), filtered and concentrated in vacuo to give tert-butyl 4-(5-ethynylpyridin-2-yl)piperazine-1-carboxylate as an orange solid (509 mg, 1.77 mmol, 100%).

$^1$H NMR (CDCl$_3$): 8.30 (d, 1H), 7.54 (dd, 1H), 6.52 (d, 1H), 3.56 (m, 8H), 3.07 (s, 1H), 1.49 (s, 9H).

To a stirred solution of tert-butyl 4-(5-ethynylpyridin-2-yl)piperazine-1-carboxylate (509 mg, 1.77 mmol), 2-Bromo-5-trifluoromethylpyridine (400 mg, 1.77 mmol), triethylamine (0.74 mL, 5.31 mmol), and cuprous iodide (135 mg, 0.71 mmol) in DMA (20 mL) at 25° C. was added tetrakistriphenylphosphine palladium (0) (102 mg, 5 mol %). The reaction was then stirred for 1 hour. Volatiles were removed in vacuo, and the residue was azeotroped with toluene (2×10 mL). The residue was then dissolved in CH$_2$Cl$_2$ (10 mL) and washed with water (10 mL). The layers were then separated and the aqueous phase extracted with CH$_2$Cl$_2$ (2×100 mL). The combined organic extracts were then dried, (MgSO$_4$), filtered and concentrated in vacuo. The residue was then purified by flash chromatography (silica gel, 25% EtOAc in hexanes) to give tert-butyl 4-(5-{[5-(trifluoromethyl)pyridin-2-yl]ethynyl}pyridin-2-yl)piperazine-1-carboxylate as a yellow solid (729 mg, 1.68 mmol, 95%).

$^1$H NMR (CDCl$_3$): 8.83 (d, 1H), 8.42 (d, 1H), 7.88, (dd, 1H), 7.67 (dd, 1H), 7.56 (d, 1H), 6.59 (d, 1H), 3.60 (m, 4H), 3.53 (m, 4H), 1.50 (s, 9H).

MS (ESI): 433.49 (MH$^+$)

To a stirred solution of tert-butyl 4-(5-{[5-(trifluoromethyl)pyridin-2-yl]ethynyl}pyridin-2-yl)piperazine-1-carboxylate (724 mg, 1.67 mmol) in CH$_2$Cl$_2$ (8 mL) at 0° C. was added trifluoroacetic acid (4 mL). The reaction was brought to room temperature and stirred for 30 minutes. Volatiles were removed in vacuo. The residue was then dissolved in CH$_2$Cl$_2$ (20 mL) and washed with aqueous sodium hydroxide solution (2M, 2×20 mL). The layers were then separated and the aqueous phase extracted with CH$_2$Cl$_2$ (3×10 mL). The combined organic extracts were then dried, (MgSO$_4$), filtered and concentrated in vacuo. The residue was dissolved in CH$_2$Cl$_2$ (50 mL), and cooled to 0° C. and treated sequentially with triethylamine (0.25 mL, 1.75 mmol) and methanesulfonyl chloride (0.14 mL, 13.5 mmol). The reaction was brought to RT and stirred for 1 hour. The reaction was then quenched with water (50 mL). The layers were separated and the aqueous phase extracted with CH$_2$Cl$_2$ (3×20 mL). The combined organic extracts were then dried, (MgSO$_4$), filtered and concentrated in vacuo to give 1-(methylsulfonyl)-4-(5-{[5-(trifluoromethyl)pyridin-2-yl]ethynyl}pyridin-2-yl)piperazine as an orange solid (445 mg, 1.08 mmol, 65%).

$^1$H NMR (CDCl$_3$): 8.85 (d, 1H), 8.45 (d, 1H), 7.90, (dd, 1H), 7.70 (dd, 1H), 7.60 (d, 1H), 6.65 (d, 1H), 3.79 (m, 4H), 3.35 (t, 4H), 2.80 (s, 3H).

MS (ESI): 411.12 (MH$^+$)

To a stirred suspension of 1-(methylsulfonyl)-4-(5-{[5-(trifluoromethyl)pyridin-2-yl]ethynyl}pyridin-2-yl)piperazine (437 mg, 1.06 mmol) in THF (10 mL) at −20° C., was added dropwise a solution of LiHMDS in THF (2.34 mL, 1.0M solution, 2.34 mmol). The resulting suspension was stirred at −20° C. for 30 minutes before being treated with diethyl chlorophosphate (0.17 mL, 1.17 mmol). The solution was then maintained at −20° C. for 15 minutes before being treated with a solution of 4-pyrimidin-2-ylbutanal (159 mg, 1.06 mmol, CAS number 260441-10-9) in THF (3 mL). The solution was stirred at −20° C. for a further 20 minutes before being quenched with saturated aqueous ammonium chloride solution (10 mL). The layers were separated and the aqueous phase extracted with ethyl acetate (3×10 mL). The combined organic extracts were then dried, (MgSO$_4$), filtered and concentrated in vacuo to give 2-((4E/Z)-5-{[4-(5-{[5-(trifluoromethyl)pyridin-2-yl]ethynyl}pyridin-2-yl)piperazin-1-yl]sulfonyl}pent-4-enyl)pyrimidine. This was used crude in the next step.

MS (ESI): 543.19 (MH$^+$)

To a stirred solution of 2-((4E/Z)-5-{[4-(5-{[5-(trifluoromethyl)pyridin-2-yl]ethynyl}pyridin-2-yl)piperazin-1-yl]sulfonyl}pent-4-enyl)pyrimidine (235 mg, 0.43 mmol), in THF (5 mL) at RT was added a solution of hydroxylamine (0.5 mL, 50% aqueous solution in water). The reaction was stirred for 3 hours at RT before being quenched with saturated aqueous ammonium chloride solution (5 mL). The layers were separated and the aqueous phase extracted with ethyl acetate (3×10 mL). The combined organic extracts were then dried, (MgSO$_4$), filtered and concentrated in vacuo. The residue was then purified by flash chromatography (silica, 10% MeOH in ethyl acetate) to give 2-(4-(hydroxyamino)-5-{[4-(5-{[5-(trifluoromethyl)pyridin-2-yl]ethynyl}pyridin-2-yl)piperazin-1-yl]sulfonyl}pentyl)pyrimidine (126 mg, 51 mmol).

MS (ESI): 576.35 (MH$^+$)

EXAMPLE 3 hydroxy{(3S)-3-phenyl-1-[({4-[4-(phenylethynyl)phenyl]piperazin-1-yl}sulfonyl)methyl]butyl}formamide

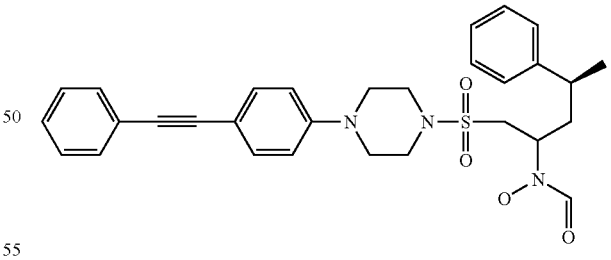

To formic acid (2.5 mL, 65 mmol) at 0° C. was added acetic anhydride (500 μL, 5.2 mmol) and the mixture was stirred at 0° C. for 10 minutes. This was added to a solution of 1-{[(4S)-2-(hydroxyamino)-4-phenylpentyl]sulfonyl}-4-[4-(phenylethynyl)phenyl]piperazine (345 mg, 0.685 mmol) in CH$_2$Cl$_2$ (5 mL) cooled to 0° C. The reaction was brought to RT and stirred for one hour. Volatiles were then removed in vacuo. The residue was then precipitated in MeOH (10 mL) and heated to 40° C. for two hours, dissolving. The solution was then cooled to RT and concentrated in vacuo. The residue was then purified by flash chromatography (silica gel, 1–2% MeOH in CH$_2$Cl$_2$) to give the title compound as a white foam (330 mg, 0.621 mmol, 91%).

$^1$H NMR (CDCl$_3$): complex mixture of 4 rotameric diastereomers.

MS (ESI): 532 (MH$^+$)

The starting material was prepared as follows:

To a solution of 1-(4-bromophenyl)piperazine hydrochloride (5.09 g, 18.3 mmol, CAS number 68104-62-1) and triethylamine (7.67 mL), in CH$_2$Cl$_2$ was added methanesulfonyl chloride (2.83 mL, 36.3 mmol) dropwise. The mixture was stirred for one hour at RT, then CH$_2$Cl$_2$ (100 mL) was added. The organics were washed with water (2×100 mL), and evaporated in vacuo to give a yellow solid which crystallised from ethanol and was washed with ether to give 1-(methylsulfonyl)-4-(4-bromophenyl)piperazine as a white powder (4.74 g, 81%).

$^1$H NMR (CDCl$_3$): 7.38 (d, 2H), 6.91 (d, 2H), 3.21 (m, 8H), 2.89 (s, 3H).

MS (ESI): 318, 320 (MH$^+$ Br isotope pattern).

To a stirred suspension of 1-(methylsulfonyl)-4-(4-bromophenyl)piperazine (5.77 g, 18.1 mmol), phenyl acetylene (3.97 mL, 36.1 mmol), Copper (I) iodide (38 mg, 0.2 mmol) and triphenylphosphine (95 mg, 0.36 mmol) in piperidine (72 mL) at 20° C. was added dichlorobis(triphenylphosphine)palladium(II) (38 mg, 54 mmol). The reaction was warmed to 105° C. and stirred for 14 hours under an inert atmosphere. Volatiles were removed in vacuo, and the solid residue was dissolved in CH$_2$Cl$_2$ (200 mL) and washed with aqueous hydrochloric acid (2M) to pH 2. The layers were then separated and the organic extract dried, (sat. Brine and MgSO$_4$), filtered and evaporated to dryness in vacuo. The residue was triturated in CH$_2$Cl$_2$, and filtered to give 1-(methylsulfonyl)-4-[4-(phenylethynyl)phenyl]piperazine as a flaky white solid (1.99 g, 5.86 mmol, 32%).

$^1$H NMR (CDCl$_3$): 7.5 (dd, 2H), 7.45 (d, 2H), 7.33, (m, 3H), 6.86 (d, 2H), 3.38 (d, 8H), 2.82 (s, 3H).

MS (ESI): 341 (MH$^+$)

To a stirred suspension of 1-(methylsulfonyl)-4-[4-(phenylethynyl)phenyl]piperazine (511 mg, 1.5 mmol) in THF (10 mL) at 40° C., was added dropwise a solution of LiHMDS in THF (3.3 mL, 11.0M solution, 3.3 mmol). The resulting suspension was stirred at −40° C. for 10 minutes before being treated with chlorotrimethylsilane (189 μL, 1.5 mmol). The solution was then maintained at −40° C. for 10 minutes before being treated with a solution of (3S)-3-phenylbutanal (267 mg, 1.8 mmol, CAS-number 53531-194) in THF (6 mL). The solution was allowed to warm to −15° C. over 1 hour before being quenched with a solution of hydroxylamine (3 mL, 50% aqueous solution in water). The reaction was stirred for 3 hours at RT. The reaction was partitioned between ethyl acetate (30 mL) and water (30 mL). The combined organic extracts were then dried (sat. brine and MgSO$_4$), filtered and concentrated in vacuo. The residue was then purified by flash chromatography (silica, 35–55% ethyl acetate in iHexane) to give 1-{[(4S)-2-(hydroxyamino)-4-phenylpentyl]sulfonyl}-4-[4-(phenylethynyl)phenyl]piperazine (351 mg, 0.697 mmol).

$^1$H NMR (CDCl$_3$): diastereomeric: 7.48 (m, 4H), 7.25 (m, 8H+CHCl$_3$), 6.87 (q, 2H), 3.35 (t, 4H), 3.23 (m, 5.5H), 2.92 (m, 1H), 2.76 (m, 0.5H), 2.02 (m, 1H), 1.83 (m, 1H), 1.33 (d, 3H).

MS (ESI): 504 (MH$^+$)

EXAMPLE 4 hydroxy [(3S)-3-phenyl-1-({[4-(4-ethynylphenyl)piperazin-1-yl]sulfonyl}methyl)butyl]formamide

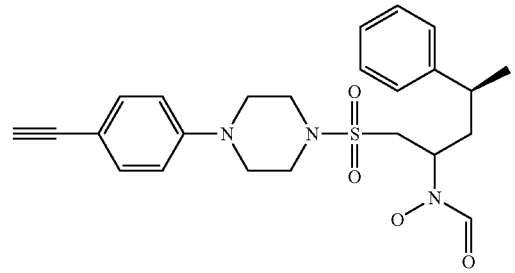

To formic acid (3.75 mL, 98 mmol) at 0° C. was added acetic anhydride (750 μL, 7.8 mmol) and the mixture was stirred at 0° C. for 10 minutes. This was added to a solution of 1-{[(4S)-2-(hydroxyamino)-4-phenylpentyl]sulfonyl}-4-[4-(trimethylsilylethynyl)phenyl]piperazine (720 mg, 94 wt %, 1.35 mmol) in CH$_2$Cl$_2$ (5 mL) cooled to 0° C. The reaction was brought quickly to RT and stirred for 20 minutes. Volatiles were then removed in vacuo, and the residue azeotroped with toluene (3×5 mL). The residue was then dissolved in MeOH (10 mL) and heated to 40° C. for two hours. The solution was then cooled to RT and concentrated in vacuo. The residue was then purified by flash chromatography (silica gel, 40–85% EtOAc in iHexane) and evaporated in vacuo. The solid was dissolved in ether/CH$_2$Cl$_2$ and the insoluble contaminant removed by filtration to give the title compound as a pink foam (90 mg, 0.171 mmol, 15%).

$^1$H NMR (CDCl$_3$): complex mixture of 4 rotameric diastereomers.

MS (ESI): 456 (MH$^+$)

The starting material was prepared as follows:

To a stirred suspension of 1-(methylsulfonyl)-4-(4-bromophenyl)piperazine (4.79 g, 15 mmol, prepared as in example 3), trimethylsilylacetylene (4.15 mL, 30 mmol), Copper (I) iodide (31 mg, 0.17 mmol) and triphenylphosphine (80 mg, 0.3 mmol) in piperidine (60 mL) at 20° C. was added dichlorobis(triphenylphosphine)palladium(II) (31 mg, 45 μmol). The reaction was warmed to 105° C. and stirred for 8 hours under an inert atmosphere. After cooling, the suspension was filtered and washed with toluene. The solid was dissolved in CH$_2$Cl$_2$, washed with water and filtered through silica, washing with CH$_2$Cl$_2$. The filtrate was concentrated and the resulting suspension filtered, washing well with CH$_2$Cl$_2$/iHexane to give 1-(methylsulfonyl)-4-[4-(trimethylsilylethynyl)phenyl]piperazine as a white powder (3.05 g, 9.06 mmol, 60

$^1$H NMR (CDCl$_3$): 7.3 (d, 2H), 6.9 (d, 2H), 3.33 (t, 4H), 3.22 (t, 4H), 2.9 (s, 3H), 0.2 (s, 9H).

MS (ESI): 337 (MH$^+$)

To a stirred suspension of 1-(methylsulfonyl)-4-[4-(trimethylsilylethynyl)phenyl]piperazine (673 mg, 2 mmol) in THF (13 mL) at −40° C., was added dropwise a solution of LiHMDS in THF (4.5 mL, 11.0M solution, 4.5 mmol). The resulting suspension was stirred at −40° C. for 10 minutes before being treated with chlorotrimethylsilane (254 μL, 2 mmol). The solution was then maintained at −40° C. for 10 minutes before being treated with a solution of (3S)-3-phenylbutanal (385 mg, 2.6 mmol, CAS number 53531-194)

in THF (8 mL). The solution was allowed to warm to −15° C. over 1 hour before being quenched with a solution of hydroxylamine (1.23 mL, 50% aqueous solution in water, 20 mmol). The reaction was stirred for 3 hours at RT. The reaction was partitioned between ethyl acetate (30 mL) and water (30 mL). The combined organic extracts were then dried, (sat. brine and MgSO$_4$), filtered and concentrated in vacuo. The residue was then purified by flash chromatography (silica, 30–40% ethyl acetate in iHexane) to give 1-{[(4S)-2-(hydroxyamino)-4-phenylpentyl]sulfonyl}-4-[4-(trimethylsilylethynyl)phenyl]piperazine (720 mg, 1.44 mmol, 68% @ 94 wt %).

$^1$H NMR (CDCl$_3$): diastereomeric: 7.39 (d, 2H), 7.27 (m, 5H+ CHCl$_3$), 6.82 (q, 2H), 3.37 (b, 4.5H), 3.25 (b, 3H), 3.18 (b, 2H), 2.92 (m, 1H), 2.75 (m, 0.5H), 2.02 (m, 1H), 1.83 (m, 1H), 1.33 (d, 3H), 0.26 (s, 9H).

MS (ESI): 500 (MH$^+$)

EXAMPLE 5

The following compounds were also prepared.

[chemical structure]

| B | R1 | M + H | Prepared using method in example |
|---|---|---|---|
| H | 2-PyrimidinylCH2CH2CH2 | 531.6 | 2 |
| 2-Pyridyl | 2-PyrimidinylCH2CH2CH2 | 536.4 | 1 |
| tert-butyl | 2-PyrimidinylCH2CH2CH2 | 515.5 | 1 |
| n-propyl | 2-PyrimidinylCH2CH2CH2 | 501.5 | 1 |
| 2-Pyridyl | 5-F-2-PyrimidinylCH2CH2 | 539.8 | 1 |
| 5-(CF3)-2-Pyridyl | 2-PyrimidinylCH2CH2CH2 | 604.4 | 2 |
| 2-Pyridyl | 2-PyrimidinylCH2CH2 | 522.1 | 1 |
| 3-Pyridyl | 2-PyrimidinylCH2CH2CH2 | 536.3 | 1 |
| 4-Pyridyl | 2-PyrimidinylCH2CH2CH2 | 536.3 | 1 |
| 2-Pyrimidinyl | 2-PyrimidinylCH2CH2CH2 | 537.5 | 7 |
| 2-Pyridyl | 5-Cl-2-PyrimidinylCH2CH2 | 556.21 | 1 |

EXAMPLE 6 hydroxy{-4-pyrimidin-2-yl-1-[({4-[5-(thien-2-ylethynyl)pyridin-2-yl]piperazin-1-yl}sulfonyl)methyl]butyl}formamide

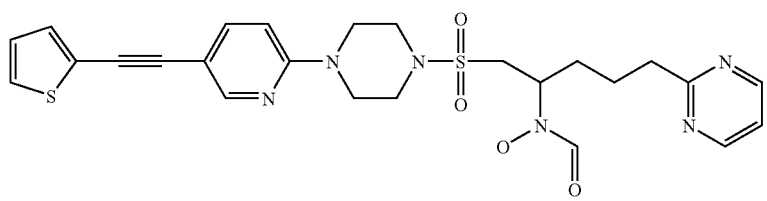

To formic acid (0.3 mL, 8 mmol) at 0° C. was added acetic anhydride (75 μL, 0.8 mmol) and the mixture was stirred at RT for 10 minutes. The reaction was then recooled to 0° C., and a solution of 2-[4-(hydroxyamino)-5-({4-[5-(thien-2-ylethynyl)pyridin-2-yl]piperazin-1-yl}sulfonyl)pentyl]pyrimidine (84 mg, 0.16 mmol) in THF (8 mL) was then added. The reaction was brought to RT and stirred for one hour. Volatiles were then removed in vacuo, and the residue azeotroped with toluene (2×5 mL). The residue was then dissolved in MeOH (10 mL) and heated to 40° C. for one hour. The solution was then cooled to RT and concentrated in vacuo. The residue was then purified by flash chromatography (silica gel, 10% MeOH in EtOAc) to give the title compound as an off-white foam (87 mg, 0.16 mmol, 54%).

$^1$H NMR (DMSO-D6, 373K): 9.38 (br s, 1H), 8.68 (d, 2H), 8.30 (d, 1H), 8.12 (br s, 1H), 7.64 (dd, 1H), 7.55 (d, 1H), 7.28 (dd, 1H), 7.22 (t, 1H), 7.09 (t, 1H), 6.85 (d, 1H), 3.68 (m, 4H), 3.41 (dd, 1H), 3.23 (m, 4H), 3.12 (dd, 1H), 2.85 (m, 3H), 1.70 (m, 4H)

MS (ESI): 541.46 (MH$^+$)

The starting material was prepared as follows:

To a stirred solution of 2-chloro-5-iodo-pyridine (CAS number 69045-79-0, 10.52 g, 43.9 mmol) and diisopropylethylamine (11.5 mL, 65.9 mmol) in DMA (200 mL) was added piperazine (15.14 g, 0.176 mol). The mixture was the heated to 120° C. for 20 hours. The solid precipitate was then filtered off, and the filtrate evaporated in vacuo. The residue was partitioned between EtOAc (100 mL) and water (100 mL) and the layers were separated. The aqueous layer was then extracted with EtOAc (2×100 mL). The combined organic extracts were then dried, (MgSO$_4$), filtered and concentrated in vacuo, to give 1-(5-iodopyridin-2-yl)piperazine as a yellow solid (10.42 g, 36 mmol, 82%).

$^1$H NMR (CDCl$_3$): 8.30 (d, 1H), 7.65 (dd, 1H), 6.45 (d, 1H), 3.46, (t, 4H), 2.97 (t, 4H).

MS (ESI): 290.29 (MH$^+$)

To a stirred solution of 1-(5-iodopyridin-2-yl)piperazine (CAS number 219635-89-9, 5.083 g, 17.6 mmol), and triethylamine (4.91 mL, 35.2 mmol) in CH$_2$Cl$_2$ (75 mL) at 0° C. was added methane sulfonyl chloride (2.04 mL, 26.4 mmol) dropwise and the resulting suspension stirred for 30 mins at room temperature. The reaction mixture was diluted with CH$_2$Cl$_2$ (200 mL) and washed twice with water (2×200 mL). The organic phase was washed with saturated brine solution (1×200 mL), dried (MgSO$_4$), filtered and concentrated in vacuo to give a dark yellow solid. This was triturated with ether, filtered and dried to give 1-(5-iodopyridin-2-yl)-4-(methylsulfonyl)piperazine as a yellow solid (5.378 g, 83%).

$^1$H NMR (CDCl$_3$): 8.33 (d, 1H), 7.70 (dd, 1H), 6.48 (d, 1H), 3.63, (t, 4H), 3.30 (t, 4H), 2.80 (s, 3H).

MS (ESI): 367.99 (MH$^+$)

To a stirred suspension of 1-(5-iodopyridin-2-yl)-4-(methylsulfonyl)piperazine (7.760 g, 21.1 mmol) in THF (150 mL) at −20° C., was added dropwise a solution of LiHMDS in THF (46.4 mL, 1.0M solution, 46.4 mmol). The resulting suspension was stirred at −20° C. for 30 minutes before being treated with diethyl chlorophosphate (3.35 mL, 23.2 mmol). The solution was then maintained at −20° C. for 15 minutes before being treated with a solution of 4-pyrimidin-2-ylbutanal (3.48 g, 23.2 mmol, CAS number 260441-10-9) in THF (20 mL). The solution was stirred at −20° C. for a further 20 minutes before being quenched with saturated aqueous ammonium chloride solution (100 mL). The layers were separated and the aqueous phase extracted with ethyl acetate (3×500 mL). The combined organic extracts were then dried, (MgSO$_4$), filtered and concentrated in vacuo. This was purified by bond-elut chromatography eluting with 25% EtOAc/hex to 50% EtOAc/hex to 100% EtOAc to give 2-((4E/Z)-5-{[4-(5-iodopyridin-2-yl)piperazin-1-yl]sulfonyl}pent-4-enyl)pyrimidine.

MS (ESI): 500.20 (MH$^+$)

To a stirred solution of 2-((4E/Z)-5-{[4-(5-iodopyridin-2-yl)piperazin-1-yl]sulfonyl}pent-4-enyl)pyrimidine (1.906 g, 3.82 mmol) in DMA (35 mL) at RT was added trimethylsilyl acetylene, (CAS number 1066-54-2, 1.08 mL, 7.64 mmol), triethylamine (1.60 mL, 11.5 mmol), CuI (291 mg, 1.53 mmol) and Pd(PPh$_3$)$_4$ (442 mg, 0.38 mmol). After stirring for 30 minutes, the DMA was removed in vacuo, and the residue diluted with EtOAc (100 mL). The dark solution was then washed with water (100 mL). The layers were separated and the aqueous phase extracted with EtOAc (3×50 mL). The combined organic extracts were then dried, (MgSO$_4$), filtered and concentrated in vacuo. The residue was then purified by flash chromatography (silica gel, 50% EtOAc in hexanes to 100% EtOAc) to give 2-{(4E/Z)-5-[(4-{5-[(trimethylsilyl)ethynyl]pyridin-2-yl}piperazin-1-yl)sulfonyl]pent-4-enyl}pyrimidine as a yellow foam (1.609 g, 3.43 mmol, 90%). This material was used semi-crude in the next step.

To a stirred solution of 2-{(4E/Z)-5-[(4-{5-[(trimethylsilyl)ethynyl]pyridin-2-yl}piperazin-1-yl)sulfonyl]pent-4-enyl}pyrimidine (1.605 g, 3.42 mmol) in THF (50 mL) was added TBAF (3.42 mL, 1 M solution, 3.42 mmol) and stirred at room temperature for 30 mins. The reaction mixture was then partitioned between water (200 mL) and EtOAc (200 mL). The layers were separated and the aqueous phase extracted twice with EtOAc (2×100 mL). The combined organics were then washed with brine (200 mL) dried, (MgSO$_4$), filtered and concentrated in vacuo. The residue was purified by bond-elut chromatography eluting with 25% EtOAc/hex to 50% EtOAc/hex to 100% EtOAc to give 2-((4E/Z)-5-{[4-(5-ethynylpyridin-2-yl)piperazin-1-yl]sulfonyl}pent-4-enyl)pyrimidine as a pale orange solid (1.065 g, 2.68 mmol, 78%).

MS (ESI): 398.10

To a stirred solution of 2-((4E/Z)-5-{[4-(5-ethynylpyridin-2-yl)piperazin-1-yl]sulfonyl}pent-4-enyl)pyrimidine (487 mg, 1.23 mmol) in DMA (20 mL) at RT was added 2-iodothiophene, (CAS number 516-12-1, 0.17 mL, 1.48 mmol), triethylamine (0.52 mL, 3.69 mmol), CuI (94 mg, 0.49 mmol) and Pd(PPh$_3$)$_4$ (142 mg, 0.13 mmol). After stirring for 1 hour, the DMA was removed in vacuo, and the residue diluted with EtOAc (100 mL). The dark solution was then washed with water (100 mL). The layers were separated and the aqueous phase extracted with EtOAc (3×50 mL). The combined organic extracts were then dried, (MgSO$_4$), filtered and concentrated in vacuo. The residue was then purified by flash chromatography (silica gel, 50% EtOAc in hexanes to EtOAc) to give 2-[(4E/Z)-5-({4-[5-(thien-2-yl-ethynyl)pyridin-2-yl]piperazin-1-yl}sulfonyl)pent-4-enyl]pyrimidine as a pale brown oil (371 mg, 0.69 mmol, 56%). This material was used semi-crude in the next step.

To a stirred solution of 2-[(4E/Z)-5-({4-[5-(thien-2-yl-ethynyl)pyridin-2-yl]piperazin-1-yl}sulfonyl)pent-4-enyl]pyrimidine (371 mg, 0.69 mmol) in THF (4 mL) was added hydroxylamine (0.4 mL, 50% aqueous solution in water) and stirred for 24 hours at room temperature. The reaction was partitioned between ethyl acetate (30 mL) and water (30 mL). The combined organic extracts were then dried (MgSO$_4$), filtered and concentrated in vacuo. The residue was then purified by bond elut chromatography (silica gel, EtOAc to 10% MeOH/EtOAc) to give 2-[4-(hydroxyamino)-5-({4-[5-(thien-2-ylethynyl)pyridin-2-yl]piperazin-1-yl}sulfonyl)pentyl]pyrimidine (84 mg, 0.16 mmol, 23%). Also recovered some isomerised SM (220 mg, 0.46 mmol, 66%) presumably formed from TBAF deprotection of 2-((4E/Z)-5-{[4-(5-ethynylpyridin-2-yl)piperazin-1-yl]sulfonyl}pent-4-enyl)pyrimidine.

$^1$H NMR (CDCl$_3$): 8.66 (m, 2H), 8.32 (d, 1H), 7.62 (dd, 1H), 7.28 (m, 2H), 7.17 (dd, 1H), 7.02 (m, 1H), 6.63 (m, 1H), 5.80 (br s, 1H), 3.74 (m, 4H), 3.46 (m, 2H), 3.41 (m, 4H), 3.19 (m, 1H), 3.04 (m, 1H), 2.81 (m, 1H), 2.00 (m, 2H), 1.69 (m, 2H).

MS (ESI): 513.41 (MH$^+$)

EXAMPLE 7

1-{[(4-{5-[(4-fluorophenyl)ethynyl]pyridin-2-yl}piperazin-1-yl)sulfonyl]methyl}-4-pyrimidin-2-ylbutyl(hydroxy)formamide

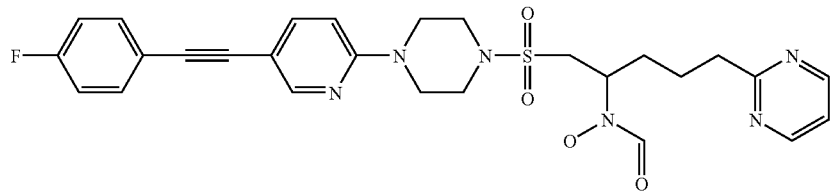

To formic acid (1.85 mL, 49.0 mmol) at 0° C. was added acetic anhydride (0.46 mL, 4.9 mmol) and the mixture was stirred at RT for 10 minutes. The reaction was then recooled to 0° C., and a solution of 2-[5-[(4-{5-[(4-fluorophenyl)ethynyl]pyridin-2-yl}piperazin-1-yl)sulfonyl]-4-(hydroxyamino)pentyl]pyrimidine (515 mg, 0.98 mmol) in THF (10 mL) was then added. The reaction was brought to RT and stirred for one hour. Volatiles were then removed in vacuo, and the residue azeotroped with toluene (2×5 mL). The residue was then dissolved in MeOH (10 mL) and heated to 40° C. for one hour. The solution was then cooled to RT and concentrated in vacuo. The white solid which precipitates upon cooling to room temperature was filtered off and dried (258 mg, 0.47 mmol, 48%).

$^1$H NMR (DMSO-D6, 373K): 9.40 (br s, 1H), 8.67 (d, 2H), 8.31 (d, 1H), 8.12 (br s, 1H), 7.68 (dd, 1H), 7.55 (m, 2H), 7.24 (t, 1H), 7.19 (t, 2H), 6.87 (d, 1H), 4.34 (br s, 1H), 3.67 (t, 4H), 3.45 (dd, 1H), 3.29 (t, 4H), 3.13 (dd, 1H), 2.89 (t, 2H), 1.72 (m, 4H)

MS (ESI): 553.54 (MH+)

The starting material was prepared as follows:

To a stirred solution of ((4E/Z)-5-{[4-(5-iodopyridin-2-yl)piperazin-1-yl]sulfonyl}pent-4-enyl)pyrimidine (988 mg, 1.98 mmol, prepared as in example 6) in DMA (25 mL) at RT was added 4-ethynylfluorobenzene, (CAS number 766-98-3, 476 mg, 3.96 mmol), triethylamine (0.83 mL, 5.94 mmol), CuI (151 mg, 0.8 mmol) and Pd(PPh₃)₄ (229 mg, 0.2 mmol). After stirring for 60 minutes, the DMA was removed in vacuo, and the residue diluted with EtOAc (100 mL). The dark solution was then washed with water (100 mL). The layers were separated and the aqueous phase extracted with EtOAc (3×50 mL). The combined organic extracts were then dried, (MgSO₄), filtered and concentrated in vacuo. The residue was then purified by bond elut chromatography (silica gel, 50% EtOAc in hexanes to 100% EtOAc) to give 2-{(4E/Z)-5-[(4-{5-[(4-fluorophenyl)ethynyl]pyridin-2-yl}piperazin-1-yl)sulfonyl]pent-4-enyl}pyrimidine as a pale brown solid (765 g, 1.56 mmol, 79%). This was used semi-crude in the next step.

To a solution of 2-{(4EZ)-5-[(4-{5-[(4-fluorophenyl)ethynyl]pyridin-2-yl}piperazin-1-yl)sulfonyl]pent-4-enyl}pyrimidine (760 mg, 1.55 mmol) in THF (10 mL) was added a solution of hydroxylamine (2 mL, 50% aqueous solution in water). The reaction was stirred for 2 hours at RT before being quenched with saturated aqueous ammonium chloride solution (5 mL). The layers were separated and the aqueous phase extracted with ethyl acetate (3×20 mL). The combined organic extracts were then dried, (MgSO₄), filtered and concentrated in vacuo. The residue was then purified by bond elut (silica, EtOAc to 10% MeOH in ethyl acetate) to give 2-[5-[(4-{5-[(4-fluorophenyl)ethynyl]pyridin-2-yl}piperazin-1-yl)sulfonyl]-4-(hydroxyamino)pentyl]pyrimidine (518 mg, 0.99 mmol, 64%).

MS (ESI): 525.33 (MH+)

EXAMPLE 8 hydroxy{(1S)-1-[({4-[5-(pyridin-2-ylethynyl)pyridin-2-yl]piperazin-1-yl}sulfonyl)methyl]-4-pyrimidin-2-ylbutyl}formamide

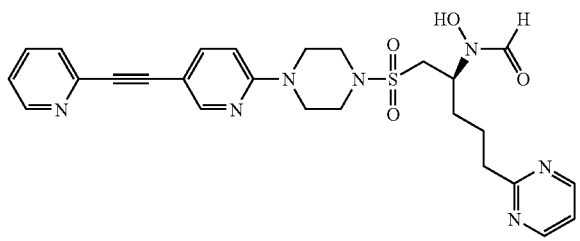

The racemic mixture, prepared as in example 1, was separated by chiral HPLC (on a Daicel Chiralpak AD column, 1 micron, 2 cm×25 cm, 20% MeOH/MeCN eluent, flow rate 9 mL/min) to give hydroxy{(1S)-1-[({4-[5-(pyridin-2-ylethynyl)pyridin-2-yl]piperazin-1-yl}sulfonyl)methyl]-4-pyrimidin-2-ylbutyl}formamide as a white solid.

¹H NMR (DMSO-D6, 373K): 9.41 (br s, 1H), 8.65 (d, 2H), 8.56 (d, 1H), 8.36 (d, 1H), 8.11 (br s, 1H), 7.79 (m, 1H), 7.71 (dd, 1H), 7.55 (d, 1H), 7.32 (m, 1H), 7.28 (dd, 1H), 6.88 (d, 1H), 3.72 (m, 4H), 3.45 (dd, 1H), 3.32 (m, 4H), 3.17 (dd, 1H), 2.92 (m, 3H), 1.77 (m, 4H)

MS (ESI): 536.45 (MH+)

EXAMPLE 9 hydroxy{1-[({4-[5-(pyridin-2-ylethynyl)pyrimidin-2-yl]piperazin-1-yl}sulfonyl)methyl]-4-pyrimidin-2-ylbutyl}formamide

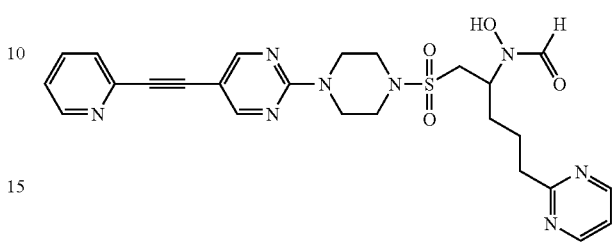

Formic acid (1.8 mL, 50 mmol) and acetic anhydride (0.5 mL, 5 mmol) were mixed together at 0° C. for 30 minutes, before being added to a solution 2-(4-{[2-(hydroxyamino)-5-pyrimidin-2-ylpentyl]sulfonyl}piperazin-1-yl)-5-(pyridin-2-ylethynyl)pyrimidine (190 mg, 0.37 mmol) in tetrahydrofuran (5 mL) and formic acid (1.8 mL) at 0° C. The reaction was allowed to reach room temperature and was stirred for 45 minutes. The reaction was then evaporated in vacuo, and azeotroped with toluene (2×5 mL). The residue was then dissolved in MeOH and heated to 45° C. for one hour. The solution was evaporated in vacuo, and the residue triturated with Et₂O to give a white solid which was collected by filtration, washed with Et₂O and dried in vacuo to give hydroxy {1-[({4-[5-(pyridin-2-ylethynyl)pyrimidin-2-yl]piperazin-1-yl}sulfonyl)methyl]-4-pyrimidin-2-ylbutyl}formamide as a white solid. (64 mg, 32%).

¹H NMR (d6-DMSO@373 k) δ 9.50 (br, s, 1H), 8.64 (m, 2H), 8.61 (m, 3H), 8.17 (br, s, 1H), 7.84 (ddd, 1H), 7.58 (d, 1H), 7.38 (m, 1H), 7.29 (dd, 1H), 4.33 (br, s, 1H), 3.96 (m, 4H), 3.48 (dd, 1H), 3.33 (m, 4H), 3.20 (dd, 1H), 2.96 (m, 2H), 1.74 (m, 4H).

MS (ESI): 537.07 (MH+)

The starting material was prepared as follows:

To a stirred solution of 5-iodo-2-piperazin-1-ylpyrimidine (7.0 g, 24.1 mmol, CAS number 95847-41-9) and triethylamine (10 mL, 72 mmol) in dichloromethane (70 mL) at 0° C. was added methanesulfonyl chloride (1.93 mL, 138 mmol) dropwise over 10 minutes. The reaction was then stirred for 30 minutes at 0° C., before being allowed to warm to room temperature and stirred for an additional 30 minutes. The reaction was then quenched with water (70 mL) and the layers were separated. The organic phase was washed with water (100 mL) and the organics were dried (MgSO₄), filtered and evaporated in vacuo. The residue was then triturated with ethyl acetate and the solid residue filtered and dried in vacuo to give 5-iodo-2-[4-(methylsulfonyl)piperazin-1-yl]pyrimidine as an off white solid (8.85 g, 24 mmol, 99%).

¹H NMR (d6-DMSO): 8.54 (s, 2H), 3.82 (m, 4H), 3.17, (m, 4H), 2.87 (s, 3H)

MS (ESI): 369.01 (MH+)

To a stirred suspension of 5-iodo-2-[4-(methylsulfonyl)piperazin-1-yl]pyrimidine (5.52 g, 15 mmol) in THF (50 mL) at –10° C., was added dropwise a solution of LiHMDS in THF (31.5 mL, 1.0M solution, 31.5 mmol). The resulting suspension was stirred at –10° C. for 20 minutes before being treated with diethyl chlorophosphate (2.24 mL, 15.5 mmol). The solution was then maintained at –20° C. for 20 minutes before being treated with a solution of 4-pyrimidin-2-ylbutanal (2.31 g, 15.5 mmol) in THF (5 mL). The solution was then maintained at −20° C. for one hour before being quenched with saturated aqueous ammonium chloride solution (50 mL). The layers were separated and the aqueous phase extracted with ethyl acetate (3×30 mL). The combined organic extracts were then dried, ($MgSO_4$), filtered and concentrated in vacuo to give a brown soild which was purified by flash chromatography (silica gel, 20% to 50% to 100% EtOAc in hexanes) to give 5-iodo-2-(4-{[(1E/Z)-5-pyrimidin-2-ylpent-1-enyl]sulfonyl}piperazin-1-yl)pyrimidine as a yellow solid (5.14 g, 68%, E:Z 1.7:1).

$^1$H NMR ($CDCl_3$): 8.58 (m, 2H), 8.33 (m, 2H), 7.18, (m, 1H), 6.73 (ddd, 1H), 6.42 (ddd)*, 6.04 (d, 1H), 5.93 (d)*, 3.82 (m, 4H), 3.11 (m, 4H), 2.94 (m, 2H), 2.63 (m)*, 2.29 (m, 2H), 1.94 (m, 2H)

* minor geometrical isomer.

MS (ESI): 501.26 ($MH^+$).

A stirred solution of 5-iodo-2-(4-{[(1E/Z)-5-pyrimidin-2-ylpent-1-enyl]sulfonyl}piperazin-1-yl)pyrimidine, (500 mg, 1 mmol), $Pd(PPh_3)_2Cl_2$ (35 mg, 0.05 mmol), CuI (76 mg, 0.4 mmol), triethylamine (0.4 mL, 3 mmol) and 2-ethynylpyridine (206 mg, 2 mmol) in THF (20 mL) was stirred at room temperature for 3 hours. The mixture was then evaporated in vacuo, and the residue purified by flash chromatography (silica gel, 1% to 2% MeOH in EtOAc) to give 5-(pyridin-2-ylethynyl)-2-(4-{[(1E/Z)-5-pyrimidin-2-ylpent-1-enyl]sulfonyl}piperazin-1-yl)pyrimidine as a white solid (224 mg, 47%).

MS (ESI): 476.39 ($MH^+$)

To a stirred solution of give 5-(pyridin-2-ylethynyl)-2-(4-{[(1E/Z)-5-pyrimidin-2-ylpent-1-enyl]sulfonyl}piperazin-1-yl)pyrimidine (220 mg, 0.46 mol) in THF (10 mL) at room temperature was added 50% aqueous hydroxylamine (2 mL) and the mixture stirred rapidly for 2 hours. The reaction was quenched by the addition of saturated ammonium chloride solution (5 mL) and the layers were then separated. The aqueous phase was then extracted with EtOAc (3×5 mL) and the combined organic extracts were then dried ($MgSO_4$), filtered and evaporated in vacuo. The white solid obtained was then purified by flash chromatography (silica gel, 50% to 100% EtOAc in hexanes), to give 5 2-(4-{[2-(hydroxyamino)-5-pyrimidin-2-ylpentyl]sulfonyl}piperazin-1-yl)-5-(pyridin-2-ylethynyl)pyrimidine as a white solid (195 mg, 0.385 mmol, 83%).

MS (ESI): 507.06 ($MH^+$)

EXAMPLE 10 hydroxy{(1S)-1-[({4-[5-(pyridin-2-ylethynyl)pyrimidin-2-yl]piperazin-1-yl}sulfonyl)methyl]-4-pyrimidin-2-ylbutyl}formamide The racemic mixture, prepared as in example 9, was separated by chiral HPLC (on a Merck Chiralpak AS-V column, 20 μm, 5 cm×25 cm, flow rate 50 mL/min, eluent=100% MeOH) to give hydroxy{(1S)-1-[({4-[5-(pyridin-2-ylethynyl)pyrimidin-2-yl]piperazin-1-yl}sulfonyl)methyl]-4-pyrimidin-2-ylbutyl}formamide as a white solid.

$^1$H NMR (d6-DMSO@373 k) δ 9.50 (br, s, 1H), 8.64 (m, 2H), 8.61 (m, 3H), 8.17 (br, s, 1H), 7.84 (ddd, 1H), 7.58 (d, 1H), 7.38 (m, 1H), 7.29 (dd, 1H), 4.33 (br, s, 1H), 3.96 (m, 4H), 3.48 (dd, 1H), 3.33 (m, 4H), 3.20 (dd, 1H), 2.96 (m, 2H), 1.74 (m, 4H).

MS (ESI): 537.07 ($MH^+$)

EXAMPLE 11

The following compounds were also prepared.

| B | R1 | M + H | Prepared using method in example |
|---|----|-------|-----------------------------------|
| 4-F—Ph | 2-PyrimidinylCH2CH2CH2 | 554.40 | 9 |
| 4-Cl—Ph | 2-PyrimidinylCH2CH2CH2 | 570.39 | 9 |
| 3-Pyridyl | 2-PyrimidinylCH2CH2CH2 | 537.39 | 9 |
| 3-Pyridyl | 5-F-2-PyrimidinylCH2CH2 | 541.36 | 9 |
| 4-F—Ph | 5-F-2-PyrimidinylCH2CH2 | 558.32 | 9 |
| 2-Pyridyl | 5-F-2-PyrimidinylCH2CH2 | 541.37 | 9 |
| 4-Cl—Ph | 5-F-2-PyrimidinylCH2CH2 | 574.20 | 9 |

What we claim is:

1. A compound of the formula I or a pharmaceutically acceptable salt or an in vivo hydrolysable ester thereof, wherein B is selected from H, $C_{1-6}$alkyl, up to C12 cycloalkyl, up to C12 aryl, and up to C12 heteroaryl; wherein B is optionally substituted by up to three groups independently selected from OH, $NO_2$, $CF_3$, CN, halogen, $SC_{1-4}$alkyl, $SOC_{1-4}$alkyl, $SO_2C_{1-4}$alkyl, $C_{1-4}$alkyl, and $C_{1-4}$alkoxy;

$L_1$ and $L_2$ are each independently selected from a direct bond and $C_{1-6}$alkyl;

$M_1$, $M_2$, $M_3$, $M_4$ and $M_5$ are each independently selected from N and C;

R1 is the group —X—Y;

X is $C_{1-6}$alkyl; and

Y is selected from up to C10 cycloalkyl, up to C10 aryl, and up to C10 heteroaryl; wherein Y is optionally substituted by up to three groups independently selected from OH, $NO_2$, $CF_3$, CN, halogen, $SC_{1-4}$alkyl, $SOC_{1-4}$alkyl, $SO_2C_{1-4}$alkyl, $C_{1-4}$alkyl, and $C_{1-4}$alkoxy.

2. A compound of the formula II or a pharmaceutically acceptable salt or an in vivo hydrolysable ester thereof,

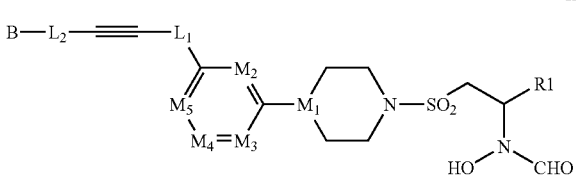

wherein
- B is selected from H, $C_{1-6}$alkyl, up to C12 cycloalkyl, up to C12 aryl, and up to C12 heteroaryl; wherein
- B is optionally substituted by up to three groups independently selected from OH, $NO_2$, $CF_3$, CN, halogen, $SC_{1-4}$alkyl, $SOC_{1-4}$alkyl, $SO_2C_{1-4}$alkyl, $C_{1-4}$alkyl, and $C_{1-4}$alkoxy;
- $L_1$ and $L_2$ are each independently selected from a direct bond and $C_{1-6}$alkyl;
- $M_1$, $M_2$, $M_3$, $M_4$ and $M_5$ are each independently selected from N and C;
- R1 is the group —X—Y;
- X is $C_{1-6}$alkyl; and
- Y is selected from up to $C_{10}$ cycloalkyl, up to $C_{10}$ aryl, and up to $C_{10}$ heteroaryl; wherein
- Y is optionally substituted by up to three groups independently selected from OH, $NO_2$, $CF_3$, CN, halogen, $SC_{1-4}$alkyl, $SOC_{1-4}$alkyl, $SO_2C_{1-4}$alkyl, $C_{1-4}$alkyl, and $C_{1-4}$alkoxy.

3. A compound as claimed in claim 1 or claim 2 or a pharmaceutically acceptable salt or an in vivo hydrolysable ester thereof, wherein B is selected from H, $C_{1-6}$alkyl, C6 aryl, and up to C6 heteroaryl.

4. A compound as claimed in claim 3 or a pharmaceutically acceptable salt or an in vivo hydrolysable ester thereof, wherein B is selected from H, $C_{2-4}$alkyl, C6 aryl, and up to C6 heteroaryl.

5. A compound as claimed in claim 4 or a pharmaceutically acceptable salt or an in vivo hydrolysable ester thereof, wherein B is up to C6 heteroaryl.

6. A compound as claimed in claim 1 or claim 2 or a pharmaceutically acceptable salt or an in vivo hydrolysable ester thereof, wherein B is not substituted or B is substituted by at least one group selected from $CF_3$, CN, halogen, and $C_{1-4}$alkyl.

7. A compound as claimed in claim 1 or claim 2 or a pharmaceutically acceptable salt or an in vivo hydrolysable ester thereof, wherein at least one of $L_1$ and $L_2$ is a direct bond.

8. A compound as claimed in claim 7 or a pharmaceutically acceptable salt or an in vivo hydrolysable ester thereof, wherein each of $L_1$ and $L_2$ is a direct bond.

9. A compound as claimed in claim 1 or claim 2 or a pharmaceutically acceptable salt or an in vivo hydrolysable ester thereof, wherein $M_1$ is N.

10. A compound as claimed in claim 1 or claim 2 or a pharmaceutically acceptable salt or an in vivo hydrolysable ester thereof, wherein at least one of $M_2$, $M_3$, $M_4$, and $M_5$ is C, and at least one of $M_2$, $M_3$, $M_4$, and $M_5$ is N.

11. A compound as claimed in claim 10 or a pharmaceutically acceptable salt or an in vivo hydrolysable ester thereof, wherein each of $M_4$ and $M_5$ is C, and at least one of $M_2$ and $M_3$ is N.

12. A compound as claimed in claim 11 or a pharmaceutically acceptable salt or an in vivo hydrolysable ester thereof, wherein $M_2$ is C or N and $M_3$ is N.

13. A compound as claimed in claim 1 or claim 2 or a pharmaceutically acceptable salt or an in vivo hydrolysable ester thereof, wherein X is $C_{2-5}$alkyl.

14. A compound as claimed in claim 13 or a pharmaceutically acceptable salt or an in vivo hydrolysable ester thereof, wherein X is $C_{2-3}$alkyl.

15. A compound as claimed in claim 1 or claim 2 or a pharmaceutically acceptable salt or an in vivo hydrolysable ester thereof, wherein Y is C6 aryl or C6 heteroaryl.

16. A compound as claimed in claim 15 or a pharmaceutically acceptable salt or an in vivo hydrolysable ester thereof, wherein Y is selected from phenyl, pyridyl, pyrimidinyl, or pyrazinyl.

17. A compound as claimed in claim 1 or claim 2 or a pharmaceutically acceptable salt or an in vivo hydrolysable ester thereof wherein Y is not substituted or Y is substituted by at least one halogen group.

18. A compound as claimed in claim 1 or a pharmaceutically acceptable salt or an in vivo hydrolysable ester thereof, wherein the compound is selected from hydroxy{-1-[({4-[5-(pyridin-2-ylethynyl)pyridin-2-yl]piperazin-1-yl}sulfonyl)methyl]-4-pyrimidin-2-ylbutyl}formamide, hydroxy[4-pyrimidin-2-yl-1-({[4-(5-{[5-(trifluoromethyl)pyridin-2-yl]ethynyl}pyridin-2-yl)piperazin-1-yl]sulfonyl}methyl)butyl]formamide, hydroxy{(3S)-3-phenyl-1-[({4-[4-(phenylethynyl)phenyl]piperazin-1-yl}sulfonyl)methyl]butyl}formamide, hydroxy[(3S)-3-phenyl-1-({[4-(4-ethynylphenyl)piperazin-1-yl]sulfonyl}methyl)butyl]formamide, hydroxy{4-pyrimidin-2-yl-1-[({4-[5-(thien-2-ylethynyl)pyridin-2-yl]piperazin-1-yl}sulfonyl)methyl]butyl}formamid, 1-{[(4-{5-[(4-fluorophenyl)ethynyl]pyridin-2-yl}piperazin-1-yl)sulfonyl]methyl}-4-pyrimidin-2-ylbutyl(hydroxy)formamide, hydroxy{(1S)-1-[({4-[5-(pyridin-2-ylethynyl)pyridin-2-yl]piperazin-1-yl}sulfonyl)methyl]-4-pyrimidin-2-ylbutyl}formamide, hydroxy {1-[({4-[5-(pyridin-2-ylethynyl)pyrimidin-2-yl]piperazin-1-yl}sulfonyl)methyl]-4-pyrimidin-2-ylbutyl}formamide, and hydroxy{(1S)-1-[({4-[5-(pyridin-2-ylethynyl)pyrimidin-2-yl]piperazin-1-yl}sulfonyl)methyl]-4-pyrimidin-2-ylbutyl}formamide.

19. A pharmaceutical composition which comprises a pharmaceutically acceptable carrier and a compound of claim 1 or claim 2 or a pharmaceutically acceptable salt or an in vivo hydrolysable ester thereof.

* * * * *

UNITED STATES PATENT AND TRADEMARK OFFICE
CERTIFICATE OF CORRECTION

PATENT NO. : 7,153,857 B2 Page 1 of 1
APPLICATION NO. : 10/485409
DATED : December 26, 2006
INVENTOR(S) : Finlay et al.

It is certified that error appears in the above-identified patent and that said Letters Patent is hereby corrected as shown below:

Claim 2, col. 27, line 25-26, change each occurrence of "$C_{10}$" to correctly read --C10--.

Signed and Sealed this

Twentieth Day of March, 2007

JON W. DUDAS
*Director of the United States Patent and Trademark Office*